(12) United States Patent
Wang et al.

(10) Patent No.: US 7,790,759 B2
(45) Date of Patent: Sep. 7, 2010

(54) GLYCYRRHETINIC ACID-30-AMIDE DERIVATIVES AND THEIR USE

(75) Inventors: Jianwu Wang, Tianjin (CN); Weiren Xu, Tianjin (CN); Jianping Wong, Tianjin (CN); Lida Tang, Tianjin (CN); Shijun Zhang, Tianjin (CN); Lijun Liu, Tianjin (CN); Yuli Wang, Tianjin (CN); Xiaowen Ren, Tianjin (CN)

(73) Assignee: Tianjin Institute of Pharmaceutical Research, Tianjin (CN)

( * ) Notice: Subject to any disclaimer, the term of this patent is extended or adjusted under 35 U.S.C. 154(b) by 267 days.

(21) Appl. No.: 12/090,169

(22) PCT Filed: Oct. 16, 2006

(86) PCT No.: PCT/CN2006/002711
§ 371 (c)(1),
(2), (4) Date: Apr. 14, 2008

(87) PCT Pub. No.: WO2007/041969
PCT Pub. Date: Apr. 19, 2007

(65) Prior Publication Data
US 2008/0214636 A1    Sep. 4, 2008

(30) Foreign Application Priority Data
Oct. 14, 2005    (CN) .................. 2005 1 0015371

(51) Int. Cl.
*A61K 31/42* (2006.01)
*C07D 261/06* (2006.01)
(52) U.S. Cl. ..................... 514/378; 548/247
(58) Field of Classification Search ................ 514/378; 548/247
See application file for complete search history.

(56) References Cited

FOREIGN PATENT DOCUMENTS

| CN | 1563073 | 1/2005 |
|----|---------|--------|
| EP | 1 449 847 | 8/2004 |
| GB | 1447162 | 8/1976 |
| GB | 1516271 | 6/1978 |
| GB | 2140809 | 12/1984 |
| WO | WO2002072084 | 9/2002 |

OTHER PUBLICATIONS

International Search Report, Corresponding to International Application No. PCT/CN2006/002711, Mailed Jan. 25, 2007.

Um et al. (2003) "Synthesis of New Glycyrrhetinic Acid (GA) Derivatives and Their Effects on Tyrosinase Activity," *Bioorg. Med. Chem.* 11:5345-5352.

EPO Official Action dated May 18, 2009, corresponding to EP Application No. 06791264.2 (1 page).

Extended European Search Report, Corresponding to European Application No. EP06791264.2, completed Feb. 19, 2009 (6 pages).

Response to May 18, 2009 EPO Official Action, filed Nov. 20, 2009, corresponding to EP Application No. 06791264.2 (23 pages).

EPO Intent to grant dated Feb. 17, 2010, corresponding to EP Application No. 06791264.2 (6 pages).

Druckexemplar (EPO approved final text) printed Apr. 27, 2009 corresponding to EP Application No. 06791264 (29 pages).

Wu et al., 1999, "Effects of Glycyrrhizin on Production of Vascular Aldosterone and Corticosterone," *Hormone Research* 51:189-192 (4 pages).

Su Xiangdong et al. (2004), "Novel 18beta-glycyrrhetinic acid analogues as potent and selective inhibitors of libeta-hydroxysteroid dehydrogenases," *Bioorganic & Medicinal Chemistry* 12:4439-4457 (19 pages).

*Primary Examiner*—Kamal A Saeed
*Assistant Examiner*—Kristin Bianchi
(74) *Attorney, Agent, or Firm*—Greenlee, Winner and Sullivan, P.C.

(57) ABSTRACT

The present invention relates to the field of a medicine for treating diseases associated with inflammation, immunity or infection, and in particular, to glycyrrhetinic acid-30-amide derivatives of general formula I and their preparation, and a pharmaceutical composition containing the same. Said derivatives and composition exhibit anti-inflammatory, analgesic, anti-allergic, cough-preventing, liver-protecting and anti-viral properties, (I)

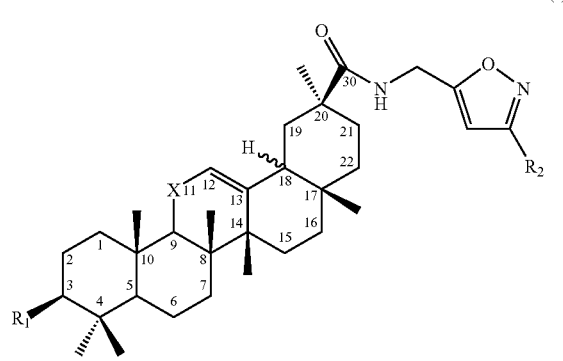

wherein each group is as defined in the description.

6 Claims, No Drawings

GLYCYRRHETINIC ACID-30-AMIDE DERIVATIVES AND THEIR USE

CROSS-REFERENCE TO RELATED APPLICATIONS

This application is the U.S. national stage application under 35 U.S.C. §371 of International Application No. PCT/CN2006/002711, filed Oct. 16, 2006, which claims benefit of Chinese Patent Application No. 200510015371.8 filed Oct. 14, 2005, all of which are hereby incorporated by reference in their entirety to the extent not inconsistent with the disclosure herein.

TECHNICAL FIELD

The present invention relates to the pharmaceutical field associated with inflammation, immunity anti-inflammatory, analgesic, anti-allergic, cough-preventing, liver-protecting and anti-viral properties and their preparation processes, and pharmaceutical compositions containing them.

BACKGROUND OF THE INVENTION

Glycyrrhizic acid and glycyrrhetinic acid have effects in relieving or eliminating inflammation, pain, allergy, and ulcer, protecting against virus, improving immunity, protecting liver and the like. Glycyrrhizic acid in injection form is now widely used for the clinical treatment of hepatitis; Carbenoxolone Sodium and zinc glycyrrhizate are used for treating gastric ulcer; and glycyrrhetinic acid in injection form is used for treating Addison's disease. Glycyrrhetinic acid, however, has a chemical structure partially similar to adrenal cortical hormone and thus produces side effects, typical of hormon pharmaceuticals, mainly aldosterone-like effects while used clinically in a large amount. These side effects lead to sodium retention and increased potassium excretion, thus resulting in edema, hypertension, hypopotassemia, etc. See Liang Qing, Pseudo-aldosteronosis caused by glycyrrhizic acid, Chinese Traditional and Herbal Drugs Communication, 1979, 6: 45-46; Wu P., Zhang Y, Liu Y, Effects of glycyrrhizin on production of vascular aldosterone and corticosterone, Horm—Res., 1999, 51 (4): 189-192.

SUMMARY OF THE INVENTION

It is an object of the invention to provide a compound having general formula I and a pharmaceutically acceptable salt thereof, which displays higher pharmaceutical activity and reduced side effects, and thus overcome the defects and the disadvantages of the prior art.

It is another object of the invention to provide a process for preparing the compound of general formula I and a pharmaceutically acceptable salt thereof.

It is still another object of the invention to provide a pharmaceutical composition containing the compound of general formula I or a pharmaceutically acceptable salt thereof as active ingredient and a pharmaceutically acceptable carrier(s), excipient(s) or diluent(s), and use thereof in anti-inflammation, analgesia, anti-allergy, prevention of cough, protection of liver, anti-virus, etc.

The invention will be described in details below in view of the object thereof.

The compound of general formula I of the invention has the following structure:

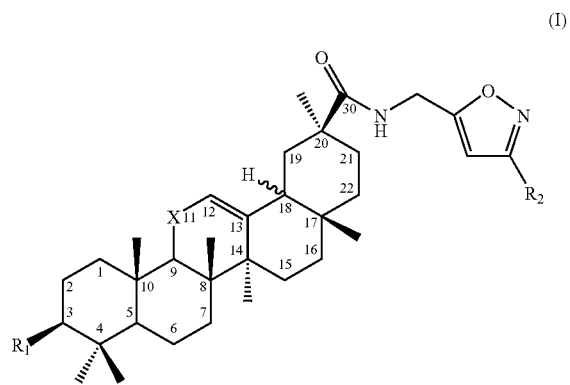

(I)

wherein $R_1$ is halogen, —OH, —$OR_1'$, —$OCOR_1'$, —$OCOCH_2CH_2COOH$, —$OCOCH_2CH_2COOR_1'$, —$NH_2$, —$NHR_1'$, —$N(R_1')_2$, —$NHCOR_1'$, —$O(CH_2)_{1-3}COOH$, or —$O(CH_2)_{1-3}COOR_1'$, wherein $R_1'$ is $C_1$-$C_5$-alkyl;

$R_2$ is H;

—$CH_2R_2'$, wherein $R_2'$ is hydrogen, halogen, hydroxyl, cyano, carboxyl, $C_1$-$C_8$-alkoxy, $C_1$-$C_5$-alkyl, or halogen-substituted $C_1$-$C_5$-alkyl;

phenyl, or phenyl which is mono- or poly-substituted by halogen, hydroxyl, cyano, carboxyl, carboxy-$C_1$-$C_3$-alkyl, $C_1$-$C_8$-alkyl, amino, nitro, $C_1$-$C_8$-alkylamino or di($C_1$-$C_8$-alkyl)amino, $C_1$-$C_8$-alkoxy, $C_1$-$C_5$-alkyl optionally substituted by halogen, or $C_1$-$C_8$-alkylcarbonyl; or 5- or 6-membered heterocyclic group containing sulphur, oxygen or nitrogen as heteroatom, or 5- or 6-membered heterocyclic group which is mono- or poly-substituted by halogen, hydroxyl, cyano, carboxyl, carboxy-$C_1$-$C_3$-alkyl, $C_1$-$C_8$-alkyl, amino, nitro, $C_1$-$C_8$-alkoxy, or $C_1$-$C_8$-alkylcarbonyl group;

X is $CH_2$ or C=O; and hydrogen in position 18 can be in R- or S-stereoisomer.

Preferred compound of formula I or a pharmaceutically acceptable salt thereof are those wherein $R_1$ is fluoro, chloro, bromo, —OH, —$OR_1'$, —$OCOR_1'$, —$OCOCH_2CH_2COOH$, —$OCOCH_2CH_2COOR_1'$, —$NH_2$, —$NHR_1'$, —$N(R_1')_2$, —$NHCOR_1'$, —$OCH_2COOH$ or —$OCH_2COOR_1'$, wherein $R_1'$ is —$CH_3$, —$CH_2CH_3$, —$CH_2CH_2CH_3$ or —$CH(CH_3)_2$;

$R_2$ is H;

$CH_2R_2'$, wherein $R_2'$ is hydrogen, fluoro, chloro, bromo, chloromethyl, chloroethyl, hydroxyl, cyano, carboxyl, methoxy, ethoxy, n-propoxy, iso-propoxy, methyl, ethyl, n-propyl or iso-propyl group;

phenyl, or phenyl which is mono- or di-substituted by fluoro, chloro, bromo, hydroxyl, cyano, carboxyl, carboxymethyl, amino, nitro, methoxy, ethoxy, iso-propoxy, methylamino, ethylamino, isopropylamino, butylamino, dimethylamino, diethylamino, methyl, ethyl, n-propyl, iso-propyl, acetyl, propionyl, or trifluoromethyl group; or imidazolyl, pyridinyl, oxazolyl, isoxazolyl, furyl, thiazolyl, pyrazolyl, thienyl, pyrrolyl,
pyridazinyl, pyrimidinyl, or pyrazinyl, or imidazolyl, pyridinyl, oxazolyl, isoxazolyl,
furyl, thiazolyl, pyrazolyl, thienyl, pyrrolyl, pyridazinyl, pyrimidinyl, or pyrazinyl which is each mono- or di-substituted by fluoro, chloro, bromo, hydroxyl, cyano, carboxyl, carboxymethyl, amino, nitro, methoxy, ethoxy, iso-propoxy, methylamino, ethylamino, isopropylamino, butylamino, methyl, ethyl, n-propyl, iso-propyl, acetyl, propionyl, or trifluoromethyl group;

X is $CH_2$ or $C=O$; and hydrogen in position 18 is in R (18-β isomer) or S (18-α isomer) configuration.

More preferred compounds of formula I are shown in the following table. In the table, all the compounds are in the form of 18-β isomers (naturally occurring configuration) unless indicated otherwise.

| No. | Nomenclature of the compound |
|---|---|
| G1 | N-[(3-p-hydroxylphenyl-isoxazol-5-yl) methyl]-glycyrrhetinamide |
| G2 | N-[(3-p-methylphenyl-isoxazol-5-yl) methyl]-glycyrrhetinamide |
| G3 | N-[(3-p-fluorophenyl-isoxazol-5-yl) methyl]-glycyrrhetinamide |
| G4 | N-[(3-o-chlorophenyl-isoxazol-5-yl) methyl]-glycyrrhetinamide |
| G5 | N-[(3-p-methoxyphenyl-isoxazol-5-yl) methyl]-glycyrrhetinamide |
| G6 | N-[(3-o-methoxyphenyl-isoxazol-5-yl) methyl]-glycyrrhetinamide |
| G7 | N-[(3-methyl-isoxazol-5-yl) methyl]-glycyrrhetinamide |
| G8 | 18-α, N-[(3-p-chlorophenyl-isoxazol-5-yl) methyl]-glycyrrhetinamide |
| G9 | N-[(3-p-trifluoromethylphenyl-isoxazol-5-yl)methyl]-glycyrrhetinamide |
| G10 | N-[(3-phenyl-isoxazol-5-yl)methyl]-glycyrrhetinamide |
| DG1 | N-[(3-p-hydroxylphenyl-isoxazol-5-yl) methyl]-11-deoxy-glycyrrhetinamide |
| DG2 | N-[(3-p-methylphenyl-isoxazol-5-yl) methyl]-11-deoxy-glycyrrhetinamide |
| DG3 | N-[(3-p-fluorophenyl-isoxazol-5-yl) methyl]-11-deoxy-glycyrrhetinamide |
| DG4 | N-[(3-o-chlorophenyl-isoxazol-5-yl) methyl]-11-deoxy-glycyrrhetinamide |
| DG5 | N-[(3-p-methoxyphenyl-isoxazol-5-yl)methyl]-3-chloro-11-deoxy-glycyrrhetinamide |
| DG6 | N-[(3-o-methoxyphenyl-isoxazol-5-yl) methyl]-11-deoxy-glycyrrhetinamide |
| DG7 | N-[(3-methyl-isoxazol-5-yl) methyl]-11-deoxy-glycyrrhetinamide |
| DG8 | N-[(3-m-chlorophenyl-isoxazol-5-yl) methyl]-11-deoxy-glycyrrhetinamide |
| DG9 | N-[(3-p-acetylphenyl-isoxazol-5-yl) methyl]-11-deoxy-glycyrrhetinamide |
| DG10 | 18-α, N-[(3-p-nitrophenyl-isoxazol-5-yl) methyl]-11-deoxy-glycyrrhetinamide |
| DG11 | N-[(3-(4-pyridin)yl-isoxazol-5-yl) methyl]-11-deoxy-glycyrrhetinamide |
| DG12 | N-{[3-(4-chloroimidazol)-5-yl-isoxazol-5-yl]methyl}-11-deoxy-glycyrrhetinamide |
| DG13 | N-{[3-(2,4-dichlorphenyl)-isoxazol-5-yl]methyl}-11-deoxy-glycyrrhetinamide |
| DG14 | N-{[3-(2,4-dimethoxyphenyl)-isoxazol-5-yl]methyl}-11-deoxy-glycyrrhetinamide |
| DG15 | N-[(3-p-trifluoromethylphenyl-isoxazol-5-yl) methyl]-11-deoxy-glycyrrhetinamide |
| DG16 | N-[(3-phenyl-isoxazol-5-yl)methyl]-11-deoxy-glycyrrhetinamide |
| RG1 | N-[(3-o-methoxyphenyl-isoxazol-5-yl) methyl]-3-acetoxy-glycyrrhetinamide |
| RG2 | N-[(3-o-methoxyphenyl-isoxazol-5-yl)methyl]-3-carboxymethoxy-glycyrrhetinamide |
| RG3 | N-[(3-o-chlorophenyl-isoxazol-5-yl) methyl]-3-ethoxy-glycyrrhetinamide |
| ADG1 | N-[(3-p-methoxyphenyl-isoxazol-5-yl) methyl]-3-amino-11-deoxy-glycyrrhetinamide |
| ADG2 | N-[(3-p-methoxyphenyl-isoxazol-5-yl)methyl]-3-diethylamino-11-deoxy-glycyrrhetinamide |
| ADG3 | N-[(3-p-methoxyphenyl-isoxazol-5-yl)methyl]-3-acetylamino-11-deoxy-glycyrrhetinamide |
| YRG1 | Sodium {N-[(3-o-methoxyphenyl-isoxazol-5-yl)methyl]glycyrrhetinamide-3-oxy}-acetate |
| YADG1 | N-[(3-p-methoxyphenyl-isoxazol-5-yl)methyl]-3-ammonium-11-deoxy-glycyrrhetinamide hydrochloride |
| YADG2 | N-[(3-p-methoxyphenyl-isoxazol-5-yl)methyl]-3-ammonium-11-deoxy-glycyrrhetinamide acetate |
| YADG3 | Triethylammonium {N-[(3-o-methoxyphenyl-isoxazol-5-yl)methyl]glycyrrhetinamide-3-oxy}-acetate |

The compound of formula I according to the invention can be synthesized through the following steps:

1. Reacting a compound of formula IIa with zinc-amalgam in the presence of dioxane and hydrochloric acid to obtain a compound of formula IIb, which can optionally be further converted to a compound of formula IIc:

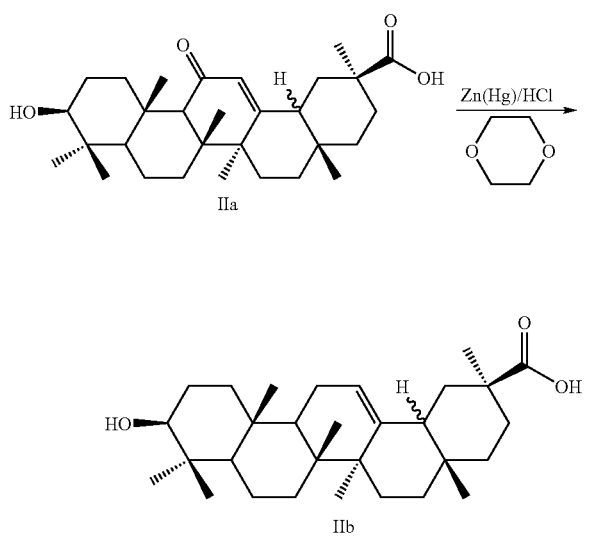

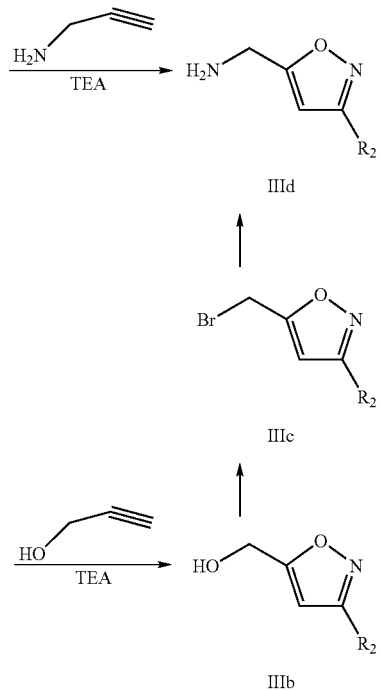

2. Reacting a compound of formula IIIa, $R_2C=NOH$, with an N-halosuccimide or sodium hypochlorite, and then, in the presence of a base (e.g. triethylamine, TEA), with propargyl amine to obtain a compound of formula IIId in a direct way; or reacting a compound of formula IIIa, $R_2C=NOH$, with an N-halosuccimide or sodium hypochlorite, and then, in the presence of a base (e.g. TEA, etc.), with propargyl alcohol to produce a compound of formula IIIb, which is subjected to bromination to produce a compound of formula IIIc, which is in turn subjected to an aminolysis reaction to obtain a compound of formula IIId;

wherein, $R_2$ is as defined above, and the compounds of formula IIIa are commercially available or can be prepared by known processes;

3. Reacting a compound of formula IIId with the compound of formula IIa or IIb to obtain a compound of formula Ia,

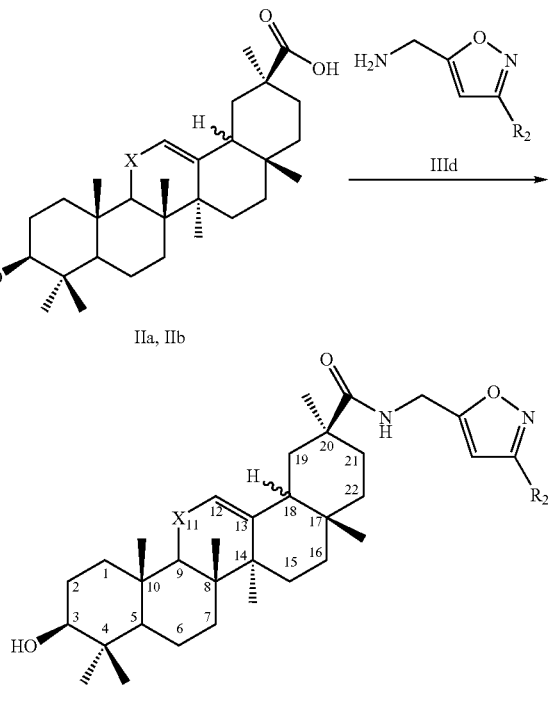

wherein X and $R_2$ are as defined above; or reacting the compound of formula IIId with the compound of formula IIc to obtain a compound of formula Ib

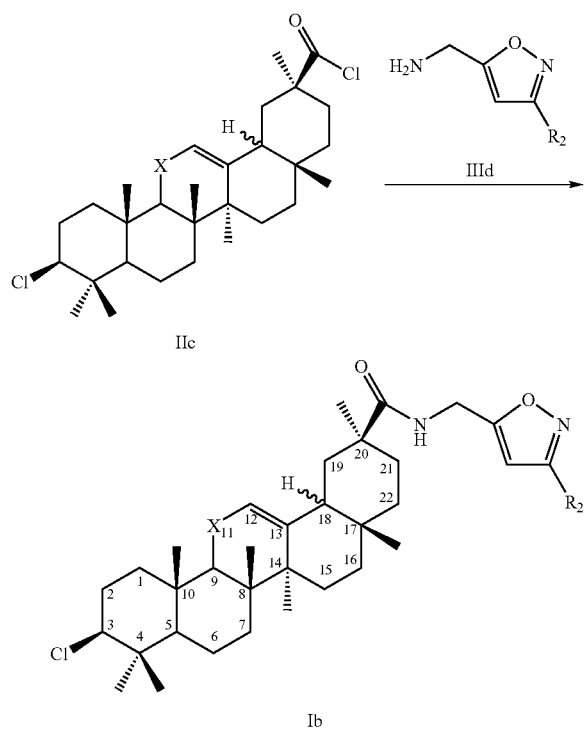

wherein X and R2 are as defined above.

By using the above compounds of formula I (Ia, or Ib), other compounds of formula I can be prepared by reacting compound Ia with an acyl halide, a bromoalkane, a carboxy-containing compound, or other reagents, or by reacting compound Ib with ammonia, an amine, an alcohol or other reagents.

The pharmaceutically acceptable salts of the compounds of formula I of the invention include, but not being limited to, for example, sodium, potassium or calcium salt, which are formed with a basic compound such as sodium hydroxide, potassium hydroxide, calcium hydroxide, sodium carbonate, etc.; those formed with a suitable organic base such as methylamine, triethylamine or meglumine; those with an inorganic acid such as hydrochloric acid, sulphuric acid, nitric acid, phosphoric acid and the like; or those with an organic acid such as formic acid, acetic acid, citric acid, oxalic acid, fumaric acid, maleic acid, an amino acid and the like.

The compounds of formula I and the salts thereof can be used as active ingredient in, for example, an anti-inflammatory agent, an anti-allergic agent, an analgesic agent, a cough-preventing agent, an anti-ulcer agent, an immunity-improving agent, a liver-protecting agent or an anti-virus agent.

The compounds of formula I and the pharmaceutically acceptable salts thereof can be formulated into a pharmaceutical composition with one or more pharmaceutically acceptable carriers, excipients, or diluents. The composition can be prepared into different formulations, for example, a solid oral formulation, a liquid oral formulation, or an injection formulation.

Said solid or liquid oral formulations include tablets, dispersible tablets, sugar-coated formulations, granules, dry powder, capsules and solution.

For solid oral formulations, lactose or starch can be used as carrier; gelatin, methylcellulose or polyvinylpyrrolidone can be used as binder; starch, sodium carboxymethycellulose, or microcrystalline cellulose can be used as disintegrant; talc powder, silica gel colloid, stearin, calcium stearate or magnesium stearate can be used as anti-blocking agent or lubricant.

The solid oral formulation can be prepared by mixing the active ingredient, a carrier and optionally a part of a disintegrant to yield a mixture; granulating the mixture with an aqueous solution, an alcoholic solution, or an aqueous alcoholic solution of the binder in an appropriate device; drying the resulting granules; and subsequently adding the remaining disintegrant, a lubricant and an anti-blocking agent to produce the formulation.

The compounds of the invention can also be administered parenterally. Preferably, the parenteral administration is achieved by injection.

The compounds of formula I have a broad range of effective dosage. For example, the dosage can be about 0.1 mg/Kg to 500 mg/Kg of body weight per day. For an adult, the most preferable dosage is in the range between 1 mg/kg and 50 mg/kg of body weight, in one dose or several doses. The actual dosage of the compounds of formula I can be determined by doctors, depending on the conditions of the patient being treated, including physical condition, administration route, age, body weight, individual drug reaction, severity of symptoms and the like.

The compounds of formula I were tested for their biological activities by the following methods.

(1) Anti-inflammatory Effect

Male or female healthy ICR mice, each weighing 18-20 g, were grouped randomly into model, positive control and test groups based on body weight, with 8-10 animals for each group. The positive group was treated by hydrocortisone in a dose of 40 mg/kg of body weight.

The compound of formula I to be tested was administered intragastrically at a concentration of 2 mg/ml in a 1% CMCNa solution, while a 1% CMCNa solution alone was administered to the model group in the same amount. 30 min after administration, 50 µl of xylene solution was added dropwise into the right ear of each mouse to cause an inflammation reaction. 30 min later, the mice were killed by breaking the cervical vertebrae. Both ears were excised immediately from the mices, and punched in the same position with a puncher having a diameter of 0.6 cm. The obtained ear piece was weighed. For each mouse, the weight ratio of swollen ear to normal ear was regarded as an indication for the degree of swelling. Biostatistical analysis was performed using the Student's t test.

(2) Analgesic Effect

Male or female healthy ICR mice, each weighing 18-22 g, were used. Each mouse was injected intraperitoneally with 0.6% acetic acid in a dose of 0.2 ml one day before the test. The mice with the writhing response occurring in the range of 10-50 times were selected. The selected mice were grouped randomly into model, positive control and test groups based on the occurrence of the writhing response, with 10 animals for each group. The positive group was treated with aspirin in a dose of 50 mg/kg of body weight.

After fasting for at least 12 h, the animals were intragastrically administrated: the animals in model group are administered only with 1% CMCNa in the same amount. 1 h after administration, the mice were intraperitoneally injected with 0.6% acetic acid in a dose of 0.2 ml per animal. After 5 min, the occurrence of the writhing responses for one mouse was recorded during a period of 15 minutes. Based on the occurrence recorded, the inhibition rate of the active ingredient for writhing response was calculated.

Inhibition rate=(means of the writhing occurrence for model group−means of the writhing occurrence for test group)/means of writhing occurrence for model group×100%.

(3) Cough-prevention

Male or female healthy ICR mice, each weighing 18-22 g, were used. They were grouped randomly into model, positive control and test groups based on body weight, with 10 animals for each group. The positive group was treated by codeine phosphate in a dose of 50 mg/kg of body weight.

After fasting for at least 12 h, the animals were intragastrically administrated: the animals in model group are administered only with 1% CMCNa in the same amount. To start the test, 1 h after administration, the mice were placed in a 500 ml container, into which a cotton ball sucking 0.3 ml of ammonia was added to cause coughing. The occurrence of cough was observed within 5 min.

Inhibition rate of cough=(the cough occurrence for model group−the cough occurrence for test group)/the cough occurrence for model group× 100%.

(4) Aldosterone-like Side Effects

Three compounds of formula I of the invention were selected to examine their subacute toxicity within one month, with dexamethasone and glycyrrhetinic acid as control. All the animals died when administrated with dexamethasone in a dose of 300 mg/kg of body weight for one week, whereas no death was observed in the case of glycyrrhetinic acid and the compound of formula I of the invention under the same conditions. Furthermore, the level of aldosterone in blood plasma was determined. The level will decrease in a negative feedback way when an agent having aldosterone-like effects is administrated. The test confirmed the aldosterone-like effects of glycyrrhetinic acid, but such effects were not shown in the case of the compound of formula I of the invention.

The results demonstrate that the compounds of formula I of the invention have high activities in anti-inflammation, analgesia, and cough-prevention. They also eliminate the aldosterone-like effects typical of glycyrrhetinic acid. The compounds of formula I of the invention exhibit improved safety and activities.

In addition, results show that the compounds of formula I of the invention have the following effects:

(1) For paracetamol/hepatitis mice models, GPT was decreased when DG6 was administrated in a dose of 100 mg/kg, which shows that the compound can protect liver.

(2) For Influenza virus A-infected mice models, death rate caused by the virus infection was decreased when DG4 was administrated in a dose of 100 mg/kg.

DETAILED DESCRIPTION OF THE INVENTION

The invention is described in detail by reference to the following examples. It is to be understood that the examples are intended to illustrate the invention and not to limit it. In light of the teaching of the invention, those skilled in the art can make various variations and modifications, which will be surely within the scope of claims of the application.

Apparatus and Reagents

BRUKER AV400 NMR spectrometer ($CDCl_3$ or DMSO-$d_6$ as internal standard). Glycyrrhetinic acid and other chemical reagents used are commercially available.

EXAMPLE 1

Preparation of 11-deoxyglycyrrhetinic acid

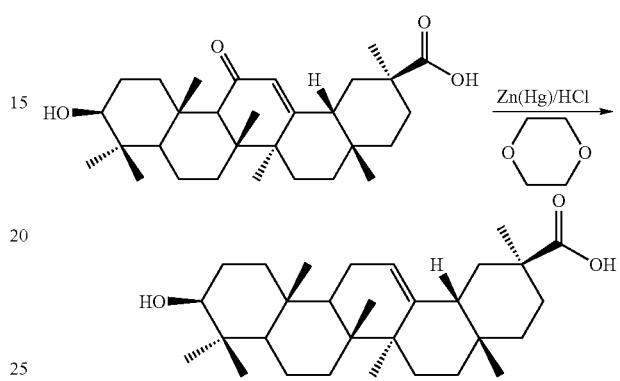

The title compound was prepared by the process as described in CA, 1984, 100, 68568e. The crude product was recrystallized from acetic acid to obtain a colorless acicular crystal. Yield: 80.86%. m.p.: 329-331° C.

$^1$HNMR (400 MHz, $CDCL_3$) δ ppm: 0.66 (s, 3H), 0.67 (s, 3H), 0.85 (s, 6H), 0.88 (s, 3H), 0.93 (m, 2H), 1.01 (m, 3H), 1.05 (s, 3H), 1.35 (m, 5H), 1.55 (m, 8H), 1.85 (m, 8H), 3.01 (m, 1H), 5.15 (s, 1H). $^{13}$CNMR (100 MHz, $CDCL_3$) δ ppm: 181.08 (—C=O), 145.23, 125.08, 68.25 ($C_3$), 64.59, 56.87, 47.38, 45.32, 45.22, 43.85, 43.52, 42.51, 39.82, 38.25, 36.25, 33.72, 32.83, 32.22, 28.79, 28.37, 27.97, 27.72, 25.30, 24.75, 19.89, 18.78, 16.87, 15.78, 15.41.

EXAMPLE 2

Preparation of 3-chloro-glycyrrhetinic acid chloride,

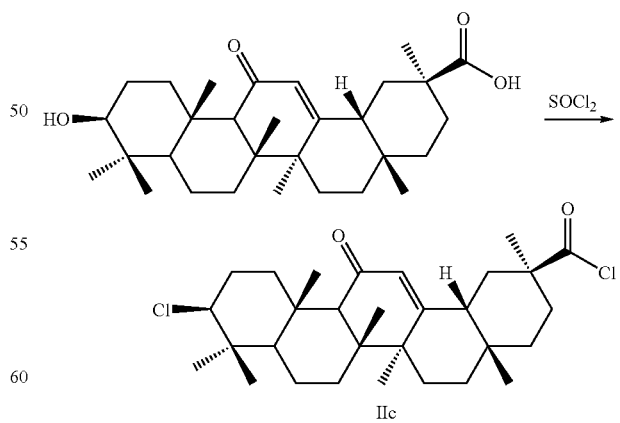

IIc 5 mmol of glycyrrhetinic acid was added to a dried erlenmeyer flask equipped with a magnetic stirrer, and then 50 ml of dichlorosulfoxide was added. The reaction mixture was stirred at room temperature and then at a slightly elevated temperature, until TLC showed no starting material remaining on TLC testing. The resulting mixture containing 3-chloro-glycyrrhetinic acid chloride was evaporated under reduced pressure to recover dichlorosulfoxide. The product was prepared immediately before use and introduced in the next step without purification.

EXAMPLE 3

Preparation of 3-chloro-11-deoxy glycyrrhetinic acid chloride

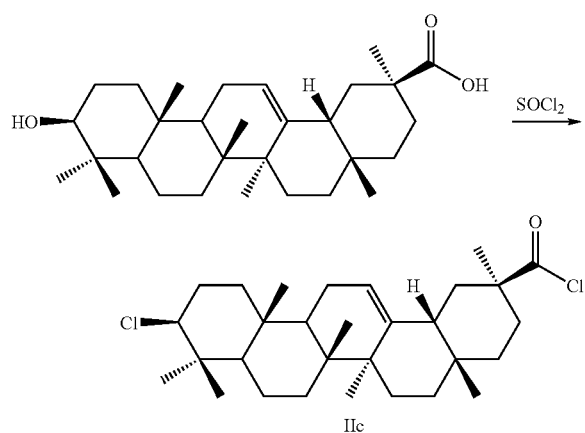

IIc 3-chloro-11-deoxyglycyrrhetinic acid chloride was prepared as described in example 2 except using 11-deoxyglycyrrhetinic acid (the product of example 1) instead of glycyrrhetinic acid. It was prepared immediately before use and introduced in the next step without purification.

EXAMPLE 4

Preparation of 3-p-chlorophenyl-5-aminomethyl-isoxazole

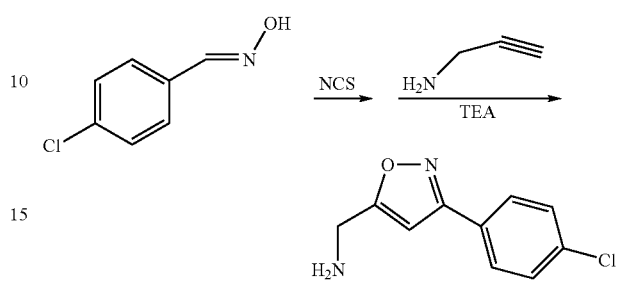

1.56 g (10 mmol) of p-chlorobenzaldoxime was dissolved in 40 ml of dried dichloromethane in a erlenmeyer flask equipped with a magnetic stirrer, and 1.7 g (12 mmol) of N-chlorosuccinimide was added slowly. The reaction mixture was stirred until completely dissolved. The system was heated slightly for 20 min. Then, 0.56 g (10 mmol) of propargyl amine was introduced and 1.2 g (12 mmol) of triethylamine was added dropwise, which caused the emission of white smog. The reaction mixture was heated under reflux for 2 h, and then purified by column chromatography on silica gel using petroleum ether (b.p. 60-90° C.)—ethyl acetate (v:v=4: 1) as eluant, to obtain 2.3 g of the product as yellow solid. The yield was 62%.

$^1$H NMR (CDCl$_3$), δ (ppm): 2.8 (s), 1H; 4.8 (s), 2H; 6.5 (s), 1H; 7.2-7.8 (m), 4H.

EXAMPLES 5-21

The compounds of formula IIId shown below were prepared as described in example 4 except using different compounds of formula IIIa instead of p-chlorobenzaldoxime in each case.

| Example No. | Compound IIIa | Compound IIId |
| --- | --- | --- |
| 5 | o-chlorobenzaldoxime | 3-o-chlorophenyl-5-aminomethyl-isoxazole |
| 6 | o-methoxybenzaldoxime | 3-o-methoxyphenyl-5-aminomethyl-isoxazole |
| 7 | m-chlorobenzaldoxime | 3-m-chlorophenyl-5-aminomethyl-isoxazole |
| 8 | acetaldoxime | 3-methyl-5-aminomethyl-isoxazole |
| 9 | p-acetyl benzaldoxime | 3-p-acetylphenyl-5-aminomethyl-isoxazole |
| 10 | p-nitrobenzaldoxime | 3-p-nitrophenyl-5-aminomethyl-isoxazole |
| 11 | p-trifluoromethylbenzaldoxime | 3-p-trifluoromethylphenyl-5-aminomethyl-isoxazole |
| 12 | p-hydroxylbenzaldoxime | 3-p-hydroxylphenyl-5-aminomethyl-isoxazole |
| 13 | p-chlorobenzaldoxime | 3-p-chlorophenyl-5-aminomethyl-isoxazole |
| 14 | p-methoxybenzaldoxime | 3-p-methoxyphenyl-5-aminomethyl-isoxazole |
| 15 | p-methylbenzaldoxime | 3-p-methylphenyl-5-aminomethyl-isoxazole |
| 16 | p-fluorobenzaldoxime | 3-p-fluorophenyl-5-aminomethyl-isoxazole |
| 17 | 4-pyridyl-formaldoxime | 3-(4-pyridin)yl-5-aminomethyl-isoxazole |
| 18 | benzaldoxime | 3-phenyl-5-aminomethyl-isoxazole |
| 19 | 4-chloro-5-formylimidazole aldoxime | 3-(4-chloroimidazol-5-yl)-5-aminomethyl-isoxazole |
| 20 | 2,4-dichlorobenzaldoxime | 3-(2,4-dichlorophenyl)-5-aminomethyl-isoxazole |
| 21 | 2,4-dimethoxybenzaldoxime | 3-(2,4-dimethoxyphenyl)-5-aminomethyl-isoxazole |

EXAMPLE 22

Preparation of N43-p-methylphenyl-isoxazol-5-yl] methyl]-11-deoxyglycyrrhetinamide (DG2)

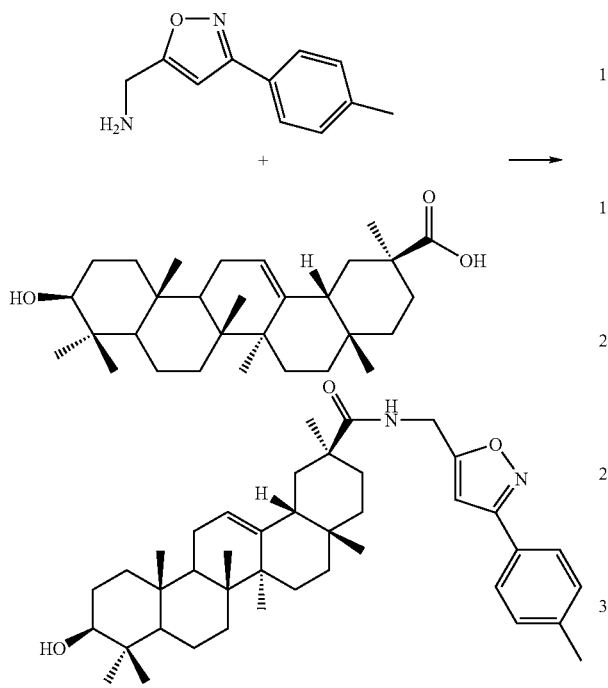

0.5 mmol of 11-deoxyglycyrrhetinic acid (the product of example 1) and 0.55 mmol of 1-hydroxybenzotrizole (HOBt) were dissolved in a mixed solution of 8 ml of dichloromethane and 2 ml of DMF. The mixture was stirred at room temperature for 10 min and then in an ice bath. A solution of 0.55 mmol of N, N'-dicyclohexylcarbodiimide (DCC) in 6 ml of dichloromethane was added dropwise to the system above. The system was stirred in an ice bath for 30 min. Then a solution of 0.75 mmol of 3-p-methylphenyl-5-aminomethyl-isoxazole (the product of example 15) in 6 ml of dichloromethane was added dropwise to the system. After being stirred in an ice bath for 2 h, the system was allowed to warm up to room temperature. The reaction continued until TLC showed the termination of the reaction. At the end of the reaction, the precipitated solid (DCU) was filtered off. The filtrate was concentrated to dryness, and the resulting crude product was taken up in a small amount of the solvent. Column chromatography using a gradient elution (ethyl acetate: petroleum ether (60-90° C.) 1:5-1:2, V/V) yielded N-[(3-p-methylphenyl-isoxazol-5-yl) methyl]-11-deoxyglycyrrhetinamide as white powder. m.p: 248-250° C. Yield: 33.02%.

$^1$H-NMR (400 MHz DMSO-$d_6$) δ ppm: 0.68 (6H, d), 0.86-0.89 (1H, m), 1.04-1.11 (6H, d), 1.29 (6H, m), 1.38 (6H, m), 1.60-1.95 (8H, m), 1.98 (1H, t, 18β-H), 2.35 (3H, s, Ar—CH3). 2.00 (1H, dt, C3-H), 4.30-4.46 (2H, m), 5.18 (1H, s, □12-H), 6.66

(1H, s, 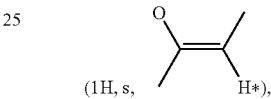 H∗), 7.30-7.70 (4H, m, Ar—H), 8.24 (1H, brs, —NH—).

EXAMPLES 23-47

The compounds of formula Ia shown below were prepared as described in example 22, except using different compounds of formula IIId instead of 3-p-methylphenyl-5-aminomethyl-isoxazole of example 4 in the reaction with compound IIa or IIb.

| Example No. | IIId | IIa, IIb | Compound Ia | No. | m.p. |
|---|---|---|---|---|---|
| 23 | 3-p-hydroxylphenyl-5-aminomethyl-isoxazole | glycyrrhetinic acid | N-[(3-p-hydroxylphenyl-isoxazol-5-yl)methyl]-glycyrrhetinamide | G1 | 208-210 |
| 24 | 3-p-methylphenyl-5-aminomethyl-isoxazole | glycyrrhetinic acid | N-[(3-p-methylphenyl-isoxazol-5-yl)methyl]-glycyrrhetinamide | G2 | 249-250 |
| 25 | 3-p-fluorophenyl-5-aminomethyl-isoxazole | glycyrrhetinic acid | N-[(3-p-fluorophenyl-isoxazol-5-yl)methyl]-glycyrrhetinamide | G3 | 243-244 |
| 26 | 3-o-chlorophenyl-5-aminomethyl-isoxazole | glycyrrhetinic acid | N-[(3-o-chlorophenyl-isoxazol-5-yl)methyl]-glycyrrhetinamide | G4 | 214-217 |
| 27 | 3-p-methoxyphenyl-5-aminomethyl-isoxazole | glycyrrhetinic acid | N-[(3-p-methoxyphenyl-isoxazol-5-yl)methyl]-glycyrrhetinamide | G5 | 247-249 |
| 28 | 3-o-methoxyphenyl-5-aminomethyl-isoxazole | glycyrrhetinic acid | N-[(3-o-methoxyphenyl-isoxazol-5-yl)methyl]-glycyrrhetinamide | G6 | 278-280 |
| 29 | 3-methyl-5-aminomethyl-isoxazole | glycyrrhetinic acid | N-[(3-methyl-isoxazol-5-yl)methyl]-glycyrrhetinamide | G7 | 156-159 |
| 30 | 3-p-chlorophenyl-5-aminomethyl-isoxazole | 18-α, glycyrrhetinic acid | 18-α, N-[(3-p-chlorophenyl-isoxazol-5-yl)methyl]-glycyrrhetinamide | G8 | 203-205 |
| 31 | 3-p-trifluoromethyl phenyl-5-aminomethyl-isoxazole | glycyrrhetinic acid | N-[(3-p-trifluoromethylphenyl-isoxazol-5-yl)methyl]-glycyrrhetinamide | G9 | 175-176 |
| 32 | 3-phenyl-5-aminomethyl-isoxazole | glycyrrhetinic acid | N-[(3-phenyl-isoxazol-5-yl)methyl]-glycyrrhetinamide | G10 | 214-216 |
| 33 | 3-p-hydroxylphenyl-5-aminomethyl-isoxazole | 11-deoxy-glycyrrhetinic acid | N-[(3-p-hydroxylphenyl-isoxazol-5-yl)methyl]-11-deoxy-glycyrrhetinamide | DG1 | 214-218 |
| 34 | 3-p-methylphenyl-5-aminomethyl-isoxazole | 11-deoxy-glycyrrhetinic acid | N-[(3-p-methylphenyl-isoxazol-5-yl)methyl]-11-deoxy-glycyrrhetinamide | DG2 | 248-250 |

-continued

| Example No. | IIId | IIa, IIb | Compound Ia | No. | m.p. □ |
|---|---|---|---|---|---|
| 35 | 3-p-fluorophenyl-5-aminomethyl-isoxazole | 11-deoxy-glycyrrhetinic acid | N-[(3-p-fluorophenyl-isoxazol-5-yl)methyl]-11-deoxy-glycyrrhetinamide | DG3 | 254-256 |
| 36 | 3-o-chlorophenyl-5-aminomethyl-isoxazole | 11-deoxy-glycyrrhetinic acid | N-[(3-o-chlorophenyl-isoxazol-5-yl)methyl]-11-deoxy-glycyrrhetinamide | DG4 | 245-248 |
| 37 | 3-o-methoxyphenyl-5-aminomethyl-isoxazole | 11-deoxy-glycyrrhetinic acid | N-[(3-o-methoxyphenyl-isoxazol-5-yl)methyl]-11-deoxy-glycyrrhetinamide | DG6 | 266-268 |
| 38 | 3-methyl-5-aminomethyl-isoxazole | 11-deoxy-glycyrrhetinic acid | N-[(3-methyl-isoxazol-5-yl)methyl]-11-deoxy-glycyrrhetinamide | DG7 | 209-211 |
| 39 | 3-m-chlorophenyl-5-aminomethyl-isoxazole | 11-deoxy-glycyrrhetinic acid | N-[(3-m-chlorophenyl-isoxazol-5-yl)methyl]-11-deoxy-glycyrrhetinamide | DG8 | 215-218 |
| 40 | 3-p-acetylphenyl-5-aminomethyl-isoxazole | 11-deoxy-glycyrrhetinic acid | N-[(3-p-acetylphenyl-isoxazol-5-yl)methyl]-11-deoxy-glycyrrhetinamide | DG9 | 231-235 |
| 41 | 3-p-nitrophenyl-5-aminomethyl-isoxazole | 18-α,11-deoxy-glycyrrhetinic acid | 18-α,N-[(3-p-nitrophenyl-isoxazol-5-yl)methyl]-11-deoxy-glycyrrhetinamide | DG10 | 245-248 |
| 42 | 3-(4-pyridin)yl-5-aminomethyl-isoxazole | 11-deoxy-glycyrrhetinic acid | N-[(3-(4-pyridin)yl-isoxazol-5-yl)methyl]-11-deoxy-glycyrrhetinamide | DG11 | 245-247 |
| 43 | 3-(4-chloroimidazol-5-yl)-5-aminomethyl-isoxazole | 11-deoxy-glycyrrhetinic acid | N-{[3-(4-chloroimidazol)-5-yl-isoxazol-5-yl]methyl}-11-deoxy-glycyrrhetinamide | DG12 | 210-212 |
| 44 | 3-(2,4-dichlorophenyl)-5-aminomethyl-isoxazole | 11-deoxy-glycyrrhetinic acid | N-{[3-(2,4-dichlorophenyl)-isoxazol-5-yl]methyl}-11-deoxy-glycyrrhetinamide | DG13 | 232-235 |
| 45 | 3-(2,4-dimethoxyphenyl)-5-aminomethyl-isoxazole | 11-deoxy-glycyrrhetinic acid | N-{[3-(2,4-dimethoxyphenyl)-isoxazol-5-yl]methyl}-11-deoxy-glycyrrhetinamide | DG14 | 189-192 |
| 46 | 3-p-trifluoromethylphenyl-5-aminomethyl-isoxazole | 11-deoxy-glycyrrhetinic acid | N-[(3-p-trifluoromethylphenyl-isoxazol-5-yl)methyl]-11-deoxy-glycyrrhetinamide | DG15 | 260-262 |
| 47 | 3-phenyl-5-aminomethyl-isoxazole | 11-deoxy-glycyrrhetinic acid | N-[(3-phenyl-isoxazol-5-yl)methyl]-11-deoxy-glycyrrhetinamide | DG16 | 245-247 |

Some of the compounds in the above table were characterized by the following $^1$H-NMR data.

G2: $^1$H-NMR (400 MHz, CDCl$_3$, TMS) δ: 0.80-0.89 (6H, m), 1.00-1.10 (6H, m), 1.13-1.21 (12H, m), 1.31-1.48 (8H, m), 1.53-1.58 (2H, m), 1.68-2.03 (6H, m), 2.03-2.07 (1H, t, 18β-H), 2.33 (s, 1H, C$_9$—H), 2.39 (s, 3H, Ar—CH$_3$), 2.78-2.81 (1H, d), 3.20-3.24 (t, 1H, C$_3$—H), 4.59-4.66 (2H, m), 5.69 (s, 1H, □$^{12}$-H), 6.10 (1H, brs, —NH—), 6.44

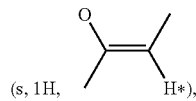

(s, 1H, H*), 7.24-7.67 (4H, m, Ar—H).

G3: $^1$H-NMR (400 MHz, DMSO-d$_6$, TMS) δ: 0.69-0.71 (6H, m), 0.91 (6H, t), 1.03-1.24 (12H, m), 1.29-1.35 (8H, m), 1.50 (d, 2H), 1.66-1.92 (6H, m), 2.07-2.09 (1H, t, 18β-H), 2.32 (s, 1H, C$_9$—H), 2.57-2.60 (d, 1H, —OH), 3.00-3.02 (m, 1H, C$_3$—H), 4.45-4.50 (2H, m), 5.51 (s, 1H, □$^{12}$-H), 6.75

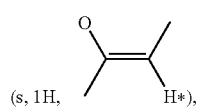

(s, 1H, H*), 7.33 (t, 2H, Ar—H), 7.89 (t, 2H, Ar—H), 8.31 (t, 1H, —NH—).

G5: $^1$H-NMR (400 MHz, DMSO-d$_6$, TMS) δ: 0.69-0.71 (d, 6H,), 0.91 (6H, m), 1.03-1.12 (12H, m), 1.29-1.35 (8H, m), 1.50 (2H, d), 1.66-1.91 (6H, m), 2.09 (t, 1H, 18β-H), 2.32 (s, 1H, C$_9$—H), 2.57 (d, 1H, —OH), 3.00 (dt, 1H, C3-H), 3.81 (s, 3H, —OCH3), 4.44 (m, 2H), 5.52 (s, 1H, □$^2$-H), 5.67

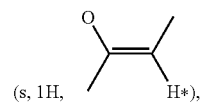

(s, 1H, H*), 7.03-7.05 (d, 2H, Ar—H), 7.75-7.77 (d, 2H, Ar—H), 8.29 (t, 1H, —NH—).

G6: $^1$H-NMR (400 MHz, DMSO-d$_6$, TMS) δ: 0.68-0.71 (d, 6H), 0.90-0.92 (6H, m), 1.11-1.16 (12H, m), 1.29-1.35 (8H, m), 1.49-1.52 (2H, d), 1.67-1.98 (6H, m), 2.06-2.09 (t, 1H, 18β-H), 2.57-2.61 (d, 1H), 2.99-3.02 (m, 1H, C$_3$—H), 3.81 (s, 3H, —OCH$_3$), 4.43-4.48 (m, 2H), 5.51 (s, 1H, □$^2$-H), 5.58

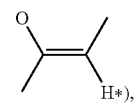

(s, 1H, H*), 7.01-7.73 (m, 4H, Ar—H), 8.29-8.31 (t, 1H, Hz,—NH—).

G9: $^1$H-NMR (400 MHz, DMSO-d$_6$, TMS) δ: 0.70-0.71 (6H, d), 0.77-0.81 (1H, m), 0.82-0.84 (5H, m), 0.85-0.93 (6H, d), 1.02-1.09 (6H, d), 1.31-1.35 (8H, m), 1.51-1.66 (6H, m)

2.08 (2H, m), 2.31 (1H, s), 2.51-2.52 (1H, d), 3.00-3.03 (1H, m), 4.31 (1H, s), 4.49-4.54 (2H, m) 5.53 (s, 1H, □²-H), 6.89

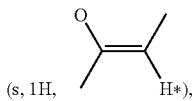
(s, 1H,            H*), 7.86-7.88 (2H, d, Ar—H), 8.07-8.09 (2H, d, Ar—H), 8.33-8.36 (1H, t, NH).

G10: ¹H-NMR (400 MHz, DMSO-d₆, TMS) δ: 0.69-0.71 (d, 6H), 0.91-0.97 (m, 6H), 1.03-1.08 (m, 12H), 1.30-1.35 (m, 8H), 1.50 (m, 2H), 1.66-1.92 (m, 6H), 2.07-2.09 (m, 1H, 18β-H), ,2.31 (s, 1H, C9-H), 2.57-2.60 (d, 1H, —OH), 3.01-3.02 (m, 1H, C₃—H), 4.45-4.50 (m, 2H), 5.52 (s, 1H, □¹²-H), 6.74

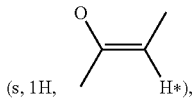
(s, 1H,            H*), 7.49-7.83 (m, 5H, Ar), 8.31 (t, 1H, —NH—).

DG2: ¹H-NMR (400 MHz, DMSO-d₆, TMS) δ: 0.68 (6H, d), 0.86-0.89 (1H, m), 1.04-1.11 (6H, d), 1.29 (6H, m), 1.38 (6H, m), 1.60-1.95 (8H, m), 1.98 (1H, t, 18β-H), 2.35 (3H, s, Ar—CH₃), 2.99 (1H, dt, C₃—H), 4.30-4.46 (2H, m), 5.18 (1H, s, □¹²-H), 6.66

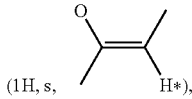
(1H, s,            H*), 7.30-7.70 (4H, m, Ar—H), 8.24 (1H, brs, —NH—).

DG3: ¹H-NMR (400 MHz, DMSO-d₆, TMS) δ: 0.68 (6H, d), 0.81-0.89 (m, 12H), 1.04 (s, 3H), 1.11 (d, 3H), 1.19-1.24 (6H, m), 1.29-1.35 (6H, m), 1.45-1.52 (8H, m), 1.99 (t, 1H, 18β-H), 2.99 (dt, 1H, C₃—H), 4.41-4.47 (2H, m), 5.18 (s, 1H, □¹²-H), 6.74

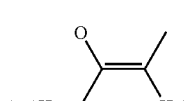
(s, 1H,            H*), 7.32-7.90 (4H, m, Ar—H), 8.24 (t, 1H, —NH—).

DG4: ¹H-NMR (400 MHz, DMSO-d₆, TMS) δ: 0.67-0.69 (6H, d), 0.81-0.92 (12H, m), 1.05 (3H, s), 1.11 (3H, s), 1.29-1.52 (6H, m), 1.79-1.87 (7H, m), 2.09 (1H, s), 2.99-3.01 (1H, m), 4.29-4.30 (1H, m), 4.42-4.48 (2H, m), 5.18 (1H, s, □¹²-H), 6.76

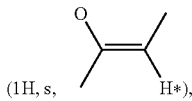
(1H, s,            H*), 7.56-7.58 (2H, d, Ar—H), 7.85-7.87 (2H, d, Ar—H), 8.22-8.25 (1H, t, —NH—).

DG6: ¹H-NMR (400 MHz, DMSO-d₆, TMS) δ: 0.68-0.70 (6H, d), 0.85-0.91 (12H, m), 1.64-1.11 (6H, m), 1.90 (1H, t, 18β-H), 1.23-1.29 (6H, m), 1.44-1.52 (6H, m), 1.60-1.81 (8H, m), 2.98-3.00 (1H, dt, C₃—H), 4.39-4.46 (2H, m), 5.20 (1H, s, □¹²-H), 6.56

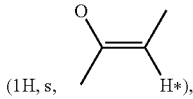
(1H, s,            H*), 7.01-7.73 (4H, m, Ar—H), 8.21-8.24 (1H, t, —NH—).

DG15: ¹H-NMR (400 MHz, DMSO-d₆, TMS) δ: 0.69-0.74 (6H, d), 0.77-0.95 (12H, m), 1.06-1.11 (6H, d), 1.27-1.52 (6H, m), 1.77-1.79 (6H, m), 1.84-2.51 (8H, m), 3.01 (1H, m), 4.29-4.30 (1H, m) 4.46-4.47 (2H, m), 5.18 (1H, s, □¹²-H), 6.86

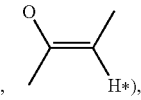
(1H, s,            H*), 7.86-7.88 (2H, d, Ar—H), 8.06-8.08 (2H, d, Ar—H), 8.26 (1H, t, —NH—).

DG16: ¹H-NMR (400 MHz, DMSO-d₆, TMS) δ: 0.67-0.70 (6H, d), 0.85-0.96 (m, 12H), 1.05 (s, 3H), 1.12 (s, 3H), 1.23-1.35 (m, 6H), 1.45-1.53 (m, 6H), 1.80-1.88 (m, 7H), 1.99 (m, 1H), 3.00 (brs, 1H), 4.30 (s, 1H), 4.42-4.49 (m, 2H), 5.19 (s, 1H, □¹²-H), 6.72

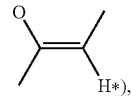
(s, 1H,            H*), 7.49-7.51 (t, 3H, Ar—H), 7.81-7.83 (t, 2H, Ar—H), 8.24 (t, 1H, —NH—).

EXAMPLE 48

Preparation of N-[(3-p-methoxyphenyl-isoxazol-5-yl)methyl]-3-chloro-11-deoxy-glycyrrhetinamide (DG5)

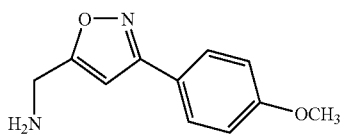

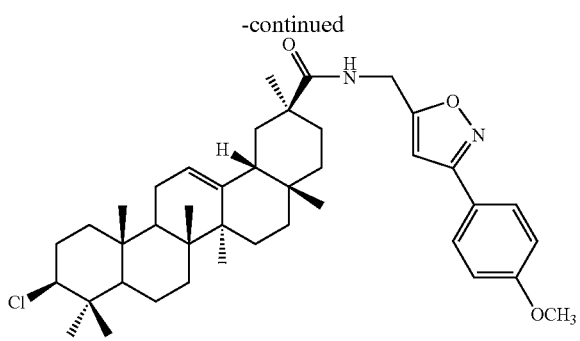

0.5 mmol of 3-chloro-11-deoxyglycyrrhetinic acid (the product of example 3) was dissolved in a mixed solution of 8 ml of dichloromethane and 2 ml of DMF and stirred in an ice bath for 30 min. Then, a solution of 0.5 mmol of 3-p-methoxyphenyl-5-aminomethyl-isoxazole (the product of example 14) in 6 ml of dichloromethane was added dropwise to the system above. 0.5 mmol of potassium carbonate was added in several portions. After being stirred in an ice bath for 2 h, the system was allowed to warm up to the room temperature. The reaction continued until TLC showed the termination of the reaction. Afterwards the precipitated solid was filtered off. The filtrate was concentrated to dryness, and the residue was taken up in a small amount of the solvent. Column chromatography using a gradient elution (ethyl acetate: petroleum ether (60-90° C.) 1:5-1:2, V/V) yielded N-[(3-p-methoxyphenyl-isoxazol-5-yl)methyl]-3-chloro -11-deoxyglycyrrhetinamide as white powder. m.p.:240-245° C.

$^1$H-NMR (400 MHz, DMSO-d$_6$) δ ppm: 0.68 (6H, d), 0.86-0.89 (1H, m), 1.06-1.14 (6H, d), 131 (6H, m), 1.39 (6H, m), 1.62-1.98 (8H, m), 1.99 (1H, t, 18β-H), 2.36 (3H, s, Ar—CH$_3$), 3.27 (1H, dt, C$_3$—H), 4.32-4.48 (2H, m), 5.20 (1H, s, $\square^2$-H), 6.64

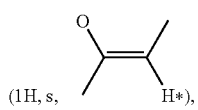

(1H, s, H*), 7.32-7.72 (4H, m, Ar—H), 8.26 (1H, brs, —NH—).

EXAMPLE 49

Preparation of N-[(3-o-methoxyphenyl-isoxazol-5-yl)methyl]-3-acetoxy-glycyrrhetinamide (RG1)

20 ml of tetrahydrofuran was added to 0.5 mmol of N-[(3-o-methoxyphenyl-isoxazol-5-yl)methyl]-glycyrrhetinamide (the product of example 28) and then an aqueous solution of 1 mmol of potassium carbonate was added. The system was cooled to 0□. Acetyl chloride (1.2 mol) was added dropwise at 0° C., and the reaction was continued until TLC showed no starting material remaining. After the addition of water, the system was extracted with dichloromethane. The removing of the solvent yielded N-[(3-o-methoxyphenyl-isoxazol-5-yl) methyl]-3-acetoxy-glycyrrhetinamide.

$^1$H-NMR (400 MHz DMSO-d$_6$) δ ppm: 0.68-0.71 (d, 6H,), 0.90-0.92 (6H, m), 1.11-1.16 (12H, m), 1.29-1.35 (8H, m), 1.49-1.52 (2H, d), 1.67-1.98 (6H, m), 2.01-2.09 (t, 4H, 18β-H), 2.57-2.61 (d, 1H), 2.99-3.02 (m, 1H, C$_3$—H), 3.82 (s, 3H, —OCH$_3$), 4.43-4.49 (m, 2H), 5.53 (s, 1H, $\square^2$-H), 5.59

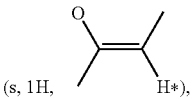

(s, 1H, H*), 7.03-7.76 (m, 4H, Ar—H), 8.29-8.31 (t, 1H, Hz, —NH—).

EXAMPLE 50

Preparation of N-[(3-o-methoxyphenyl-isoxazol-5-yl)methyl]-3-carboxymethoxy-glycyrrhetinamide (RG2)

20 ml of tetrahydrofuran was added to 1 mmol of N-[(3-o-methoxyphenyl-isoxazol-5-yl) methyl]-glycyrrhetinamide (the product of example 28), and an aqueous solution of 1 mol of potassium carbonate was added. The system was cooled to 0° C. Ethyl bromoacetate (1.2 mol) was added dropwise at 0° C., and the reaction was continued at room temperature until TLC showed no starting material remaining. After the addition of water and then an aqueous solution of 1 mol of potassium carbonate, the reaction was stirred at a slightly elevated temperature. After the end of deesterification, the solution was acidified and extracted with dichloromethane. The removing of the solvent yielded N-[(3-o-methoxyphenyl-isoxazol-5-yl)methyl]-3-carboxymethoxy-glycyrrhetinamide.

$^1$H-NMR (400 MHz, DMSO-d$_6$) δ ppm: 0.68-0.71 (d, 6H,), 0.90-0.92 (6H, m), 1.11-1.16 (12H, m), 1.29-1.35 (8H, m), 1.49-1.52 (2H, d), 1.67-1.98 (6H, m), 2.06-2.09 (t, 1H, 18β-H), 2.57-2.61 (d, 1H), 2.99-3.02 (m, 1H, C$_3$—H), 3.81 (s, 3H, —OCH$_3$), 4.01 (s, 2H, —COCH$_3$O—), 4.46-4.49 (m, 2H), 5.54 (s, 1H, $\square^{12}$-H), 5.57

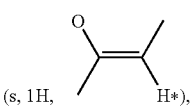

(s, 1H, H*), 7.11-7.83 (m, 4H, Ar—H), 8.39-8.41 (t, 1H, Hz, —NH—).

EXAMPLE 51

Preparation of N-[(3-p-methoxyphenyl-isoxazol-5-yl)methyl]-3-amino-11-deoxy glycyrrhetinamide (ADG1)

0.5 mmol of N-[(3-p-methoxyphenyl-isoxazol-5-yl)methyl]-3-choloro-11-deoxy glycyrrhetinamide (the product of example 48) was dissolved in 8 ml of dichloromethane. Ammonia gas was introduced with stirring at room temperature, and if necessary, at a slightly elevated temperature. The reaction mixture was stirred until TLC showed the termination of the reaction. Afterwards, the precipitated solid was filtered off. The filtrate was concentrated to dryness, and the residue was recrystallized from a mixed solution of ethanol and water to yield N-[(3-p-methoxyphenyl-isoxazol-5-yl) methyl]-3-amino-I 1-deoxyglycyrrhetinamide.

$^1$H-NMR (400 MHz, DMSO-d$_6$) δ ppm: 0.68 (6H, d), 0.86-0.89 (1H, m), 1.06-1.14 (6H, d), 1.31 (6H, m), 1.39 (6H, m), 1.66-1.99 (8H, m), 1.99 (1H, t, 18β-H), 2.36 (3H, s, Ar—CH3), 2.67 (1H, dt, C3-H), 4.32-4.48 (2H, m), 5.20 (1H, s, □12-H), 6.64

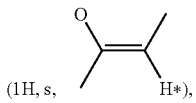

(1H, s, H*), 7.32-7.72 (4H, m, Ar—H), 8.26 (1H, brs, —NH—).

EXAMPLE 52

Preparation of N-[(3-p-methoxyphenyl-isoxazol-5-yl)methyl]-3-diethylamino-11-deoxyglycyrrhetinamide (ADG2)

0.5 mmol of the product of example 51 was dissolved in 10 ml of dichloromethane. 1.2 mmol of diethylamine was added. Then the reaction mixture was stirred at room temperature and a solution of 1.2 mmol of ethyl bromide in dichloromethane was added dropwise. The reaction mixture was stirred until TLC showed the termination of the reaction. Afterwards the precipitated solid was filtered off. The filtrate was concentrated to dryness and the residue was recrystallized from a mixed solution of ethanol and water to yield N-[(3-p-methoxyphenyl-isoxazol-5-yl)methyl]-3-diethylamino-11-deoxyglycyrrhetinamide.

$^1$H-NMR (400 MHz, DMSO-d$_6$) δ ppm: 0.68 (6H, d), 0.86-0.89 (1H, m), 1.01-1.18 (12H), 1.32 (6H, m), 1.39 (6H, m), 1.66-1.99 (8H, m), 2.01 (1H, t, 18β-H), 2.33 (3H, s, Ar—CH$_3$), 2.35-2.65 (5H, C$_3$—H and the methylene in diethylamino group ), 4.32-4.48 (2H, m), 5.21 (1H, s, □$^{12}$-H), 6.63

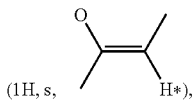

(1H, s, H*), 7.32-7.75 (4H, m, Ar—H), 8.27 (1H, brs, —NH—)

EXAMPLE 53

Preparation of N-[(3-p-methoxyphenyl-isoxazol-5-yl)methyl]-3-acetylamino-11-deoxyglycyrrhetinamide (ADG3)

0.5 mmol of the product of example 51 was dissolved in 10 ml of dichloromethane. 0.6 mmol of triethylamine was added. Then the reaction mixture was stirred at room temperature and 0.6 mmol of acetyl chloride was added dropwise. The reaction mixture was stirred until TLC showed the termination of the reaction. Afterwards, the resultant liquid was concentrated to dryness, and the residue was recrystallized from a mixed solution of ethanol and water to yield N-[(3-p-methoxyphenyl-isoxazol-5-yl)methyl]-3-acetylamino-11-deoxyglycyrrhetinamide.

$^1$H-NMR (400 MHz, DMSO-d$_6$) δ ppm: 0.69 (6H, d), 0.87-0.91 (1H, m), 1.03-1.21 (6H), 1.33 (6H, m), 1.39 (6H, m), 1.66-1.99 (8H, m), 1.99-2.03 (4H, 18β-H and the hydrogen in the acetylamino group), 2.36 (3H, s, Ar—CH$_3$), 2.33-2.41 (1H, C$_3$—H), 4.32-4.48 (2H, m) 5.22 (1H, s, □$^2$-H), 6.66

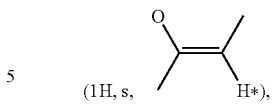

(1H, s, H*), 7.34-7.74 (4H, m, Ar—H), 8.28 (1H, brs, —NH—).

EXAMPLE 54

Preparation of N-[(3-o-chlorophenyl-isoxazol-5-yl) methyl]-3-ethoxy-glycyrrhetinamide (RG3)

20 ml of tetrahydrofuran was added to 1 mmol of N-[(3-o-chlorophenyl-isoxazol-5-yl) methyl]-glycyrrhetinamide (the product of example 26), and then an aqueous solution of 1 mol of potassium carbonate was added. The system was cooled to 0□. Ethyl bromide (1.2 mol) was added dropwise at 0□. After the addition, the reaction was continued at room temperature until TLC showed no starting material remaining. The reaction mixture was extracted with dichloromethane, followed by the recovery of the solvent to yield N-[(3-o-chlorophenyl-isoxazol-5-yl)methyl]-3-ethoxy-glycyrrhetinamide. Yield: 35%. m.p.: 198-201□.

EXAMPLE 55

Preparation of Sodium {N-[(3-o-methoxyphenyl-isoxazol-5-yl)methyl]glycyrrhetinamide-3-oxy}acetate (YRG1)

5 ml of an aqueous solution containing 0.55 mmol of NaOH was added to 0.5 mmol of N-[(3-o-methoxyphenyl-isoxazol-5-yl)methyl]-3-carboxymethoxy-glycyrrhetinamide (the product of example 50). The mixture was stirred at a slightly elevated temperature until dissolution. An appropriate amount of ethanol was added, and the system was allowed to stand at 0□ for crystallization. The resulting crystal was filtered out and dried to yield Sodium {N-[(3-o-methoxyphenyl-isoxazol-5-yl)methyl]glycyrrhetinamide-3-oxy}acetate Yield: about 60%.

EXAMPLE 56

Preparation of the salt of triethylammonium {N-[(3-o-methoxyphenyl-isoxazol-5-yl)-methyl]glycyrrhetinamide-3-oxy}acetate (YADG3)

10 ml of dichloromethane was added to 0.5 mmol of N-[(3-o-methoxyphenyl-isoxazol-5-yl) methyl]-3-carboxymethoxy-glycyrrhetinamide (the product of example 50), followed by the addition of 0.55 mmol of triethylamine. The reaction mixture was stirred under reflux for 1 h and allowed to cool to room temperature for crystallization. The resulting crystal was filtered out, and dried to yield the salt of triethylammonium {N-[(3-o-methoxyphenyl-isoxazol-5-yl)-methyl]glycyrrhetinamide-3-oxy}acetate. Yield: about 5 0%.

EXAMPLE 57

Preparation of N-[(3-p-methoxyphenyl-isoxazol-5-yl)methyl]-3-ammonium-11-deoxyglycyrrhetinamide hydrochloride (YADG1)

10 ml of a 5% aqueous solution of HCl was added to 0.5 mmol of N-[(3-p-methoxyphenyl-isoxazol-5-yl)methyl]-3- amino-11-deoxyglycyrrhetinamide (the product of example 51). The mixture was stirred at a slightly elevated temperature to give a solution. An appropriate amount of ethanol was added, and the system was allowed to stand at 0□ for crystallization. The resulting crystal was filtered out, and dried to yield N-[(3-p-methoxyphenyl-isoxazol-5-yl)methyl]-3-ammonium-11-deoxyglycyrrhetinamide hydrochloride. Yield: about 65%.

EXAMPLE 58

Preparation of N-[(3-p-methoxyphenyl-isoxazol-5-yl)methyl]-3-ammonium-11-deoxyglycyrrhetinamide acetate (YADG2)

10 ml of dichloromethane was added to 0.5 mmol of N-[(3-p-methoxyphenyl-isoxazol-5-yl) methyl]-3-amino-11-deoxyglycyrrhetinamide (the product of example 51), followed by the addition of 2 ml of acetic acid. The system was stirred under reflux for 1 h and then allowed to cool to the room temperature for crystallization. The resulting crystal was filtered out, and dried to yield N-[(3-p-methxoyphenyl-isoxazol-5-yl)methyl]-3-ammonium-11-deoxyglycyrrhetinamide acetate. Yield: about 60%.

PHARMACEUTICAL PREPARATION EXAMPLES

Example 1

Preparation of a tablet comprising the compound of the invention as active ingredient in an amount of 100 mg per tablet:

|   | Amount per tablet |
|---|---|
| Test sample G4 | 100 mg |
| Microcrystalline cellulose | 55 mg |
| Starch | 45 mg |
| Hydroxymethylcellulose | 4 mg |
| Sodium carboxymethyl starch | 5 mg |
| Magnesium stearate | 1 mg |
| Talc powder | 1 mg |

All the ingredients were used in the above-mentioned amounts. The active ingredient, starch and cellulose were sieved and mixed sufficiently. The mixture powder was mixed with an aqueous hydroxymethylcellulose solution and then sieved to obtain wet granules. The granules were dried at 50-60° C. The pre-sieved sodium carboxymethyl starch, magnesium stearate and talc powder were added to the granules and then pressed to obtain tablets.

Example 2

|   | Preparation of injection |
|---|---|
| Test RG2 | 100 mg |
| Sodium citrate | 50 mg |
| PEG3000 | 10 mg |
| Sodium hydroxide | an appropriate amount |
| Distilled water | 10 ml |

The mixture was adjusted to pH 7.5-8.5, and then filtered. The filtrate at a concentration of 1 mg/ml was divided into aliquots of 2 ml per ampoule and then sterilized to yield injections.

The activity data of the compounds of formula I of the invention are shown below.

Data of Anti-inflammatory Activity

| Group | Dose | Swelling degree of the swollen ear model (%) ($\bar{x} \pm sd$) |
|---|---|---|
| model | — | 116.1 ± 33.4 |
| hydrocortisone | 40 mg/kg | 55.7 ± 35.4** |
| G2 | 40 mg/kg | 68.6 ± 29.5** |
| G3 | 40 mg/kg | 60.8 ± 27.9** |
| G6 | 40 mg/kg | 53.4 ± 35.2** |
| DG2 | 40 mg/kg | 80.2 ± 18.8* |
| DG3 | 40 mg/kg | 56.1 ± 28.3** |
| DG6 | 40 mg/kg | 64.4 ± 29.2** | n: 8-10;

Note:

*$p < 0.05$,

**$p < 0.01$ compared to model group

Data of Analgesic Activity

| Group | Dose (mg/kg) | Writhing occurrence ($\bar{x} \pm s$) | Inhibition rate of writhing response (%) |
|---|---|---|---|
| model | 50 | 20.33 ± 17.52 | — |
| G1 | 50 | 16.33 ± 10.57 | 19.7 |
| DG4 | 50 | 6.56 ± 6.19* | 67.8 |
| DG6 | 50 | 8.00 ± 6.48* | 60.7 |
| DG3 | 50 | 18.33 ± 13.56 | 9.8 |
| DG7 | 50 | 15.78 ± 12.43 | 22.4 |
| DG8 | 50 | 15.89 ± 16.67* | 21.9 |
| aspirin | 50 | 5.44 ± 5.87* | 73.2 | n = 10;

*$p < 0.05$,

**$p < 0.01$, compared to model group

Data of Cough-preventing Activity

| Group | Dose (mg/kg) | Cough occurrence ($\bar{x} \pm sd$) | Inhibition rate of cough (%) |
|---|---|---|---|
| model | 50 | 27.80 ± 11.70 | — |
| G1 | 50 | 28.20 ± 15.39 | −1.44 |
| DG4 | 50 | 18.80 ± 7.04* | 32.37 |
| DG6 | 50 | 22.60 ± 9.56 | 18.71 |
| DG3 | 50 | 17.70 ± 7.10* | 36.33 |
| DG7 | 50 | 20.40 ± 14.31 | 26.62 |
| DG8 | 50 | 17.90 ± 8.21* | 35.61 |
| RG1 | 50 | 17.64 ± 6.34* | 36.55 |
| codeine phosphate | 50 | 8.40 ± 8.95** | 69.78 | n = 10;

*$p < 0.05$,

**$p < 0.01$, compared to model group

Data of Aldosterone-like Side Effects

| Group | Dose (mg/kg) | Aldosterone level in blood plasma (ng/ml) ($\bar{\chi}$ ± sd) |
|---|---|---|
| blank | — | 705.2 ± 464.9 |
| glycyrrhetinic acid | 300 mg/kg | 68.3 ± 12.5* |
| DG3 | 300 mg/kg | 971.8 ± 359.1 |
| DG8 | 300 mg/kg | 890.4 ± 220.7 |
| DG4 | 300 mg/kg | 987.8 ± 342.2 | n = 8;
*p < 0.05 compared to model group

The invention claimed is:

1. A compound of general formula I,

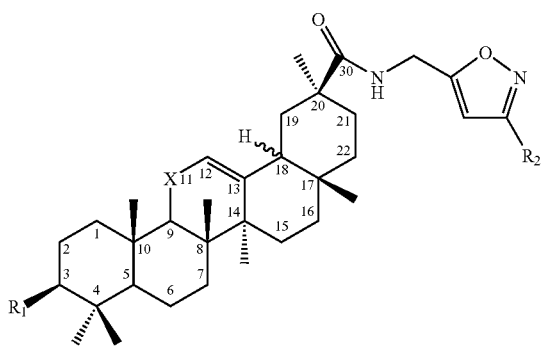

(I)

wherein, $R_1$ is halogen, —OH, —OR$_1$', —OCOR$_1$', —OCOCH$_2$CH$_2$COOH, —OCOCH$_2$CH$_2$COOR$_1$', —NH$_2$, —NHR$_1$', —N(R$_1$')$_2$, —NHCOR$_1$', —O(CH$_2$)$_{1-3}$COOH or —O(CH$_2$)$_{1-3}$COOR$_1$', wherein R$_1$', is C$_1$-C$_5$-alkyl;

$R_2$ is phenyl, or phenyl which is mono- or poly-substituted by halogen, hydroxyl, cyano, carboxyl, carboxy-C$_1$-C$_3$-alkyl, C$_1$-C$_8$-alkyl, amino, nitro, C$_1$-C$_8$-alkylamino or di(C$_1$-C$_8$-alkyl)amino, C$_1$-C$_8$-alkoxy, C$_1$-C$_5$-alkyl optionally substituted by halogen, or C$_1$-C$_8$-alkylcarbonyl; or 5- or 6-membered heterocyclic group containing sulphur, oxygen, or nitrogen as heteroatom, or 5- or 6-membered heterocyclic group which is mono- or poly-substituted by halogen, hydroxyl, cyano, carboxyl, carboxy-C$_1$-C$_3$-alkyl, C$_1$-C$_8$-alkyl, amino, nitro, C$_1$-C$_8$-alkoxy, or C$_1$-C$_8$-alkylcarbonyl group;

X is CH$_2$ or C=O; and hydrogen in position 18 is in R— or S-stereoisomer;

or a pharmaceutically acceptable salt thereof.

2. The compound of formula I according to claim 1, wherein $R_1$ is fluoro, chloro, bromo, —OH, —OR$_1$', —OCOR$_1$', —OCOCH$_2$CH$_2$COOH, —OCOCH$_2$CH$_2$COOR$_1$', —NH$_2$, —NHR$_1$', —N(R$_1$')$_2$, —NHCOR$_1$', —OCH$_2$COOH or —OCH$_2$COOR$_1$', wherein R$_1$' is —CH$_3$, —CH$_2$CH$_3$, —CH$_2$CH$_2$CH$_3$ or —CH(CH$_3$)$_2$;

$R_2$ is phenyl, or phenyl which is mono- or di-substituted by fluoro, chloro, bromo, hydroxyl, cyano, carboxyl, carboxymethyl, amino, nitro, methoxy, ethoxy, iso-propoxy, methylamino, ethylamino, isopropylamino, butylamino, dimethylamino, diethylamino, methyl, ethyl, n-propyl, iso-propyl, acetyl, propionyl, or trifluoromethyl group; or imidazolyl, pyridyl, oxazolyl, isoxazolyl, furyl, thiazolyl, pyrazolyl, thienyl, pyrrolyl, pyridazinyl, pyrimidinyl, or pyrazinyl, or imidazolyl, pyridyl, oxazolyl, isoxazolyl, furyl, thiazolyl, pyrazolyl, thienyl, pyrrolyl, pyridazinyl, pyrimidinyl, or pyrazinyl which is each mono- or di-substituted by fluorine, chlorine, bromine, hydroxyl, cyano, carboxyl, carboxymethyl, amino, nitro, methoxy, ethoxy, iso-propoxy, methylamino, ethylamino, isopropylamino, butylamino, methyl, ethyl, n-propyl, iso-propyl, acetyl, propionyl, or trifluoromethyl group;

X is CH$_2$ or C=O; and hydrogen in position 18 is in R or S configuration;

or a pharmaceutically acceptable salt thereof.

3. The compound of formula I according to claim 1, which is selected from the group consisting of N-[(3-p-hydroxylphenyl-isoxazol-5-yl) methyl]-glycyrrhetinamide, N-[(3-p-methylphenyl-isoxazol-5-yl) methyl]-glycyrrhetinamide, N-[(3-p-fluorophenyl-isoxazol-5-yl) methyl]-glycyrrhetinamide, N-[(3-o-chlorophenyl-isoxazol-5-yl) methyl]-glycyrrhetinamide, N-[(3-p-methoxyphenyl-isoxazol-5-yl) methyl]-glycyrrhetinamide, N-[(3-o-methoxyphenyl-isoxazol-5-yl) methyl]-glycyrrhetinamide, N-[(3-methyl-isoxazol-5-yl) methyl]-glycyrrhetinamide, 18-α, N-[(3-p-chlorophenyl-isoxazol-5-yl) methyl]-glycyrrhetinamide, N-[(3-p-trifluoromethylphenyl-isoxazol-5-yl)methyl]-glycyrrhetinamide, N-[(3-phenyl-isoxazol-5-yl)methyl]-glycyrrhetinamide, N-[(3-p-hydroxylphenyl-isoxazol-5-yl) methyl]-11-deoxy-glycyrrhetinamide, N-[(3-p-methylphenyl-isoxazol-5-yl) methyl]-11-deoxy-glycyrrhetinamide, N-[(3-p-fluorophenyl-isoxazol-5-yl) methyl]-11-deoxy-glycyrrhetinamide, N-[(3-o-chlorophenyl-isoxazol-5-yl) methyl]-11-deoxy-glycyrrhetinamide, N-[(3-p-methoxyphenyl-isoxazol-5-yl) methyl]-3-chloro-11-deoxy- glycyrrhetinamide, N-[(3-o-methoxyphenyl-isoxazol-5-yl) methyl]-11-deoxy-glycyrrhetinamide, N-[(3-methyl-isoxazol-5-yl) methyl]-11-deoxy-glycyrrhetinamide, N-[(3-m-chlorophenyl-isoxazol-5-yl) methyl]-11-deoxy-glycyrrhetinamide, N-[(3-p-acetylphenyl-isoxazol-5-yl) methyl]-11-deoxy-glycyrrhetinamide, 18-α, N-[(3-p-nitrophenyl-isoxazol-5-yl) methyl]-11-deoxy-glycyrrhetinamide, N-[(3-(4-pyridin) yl-isoxazol-5-yl) methyl]-11-deoxy-glycyrrhetinamide, N-{[3-(4-chloroimidazol)-5-yl-isoxazol-5-yl] methyl}-11-deoxy- glycyrrhetinamide, N-{[3-(2, 4-dichlorophenyl)-isoxazol-5-yl] methyl}-11-deoxy- glycyrrhetinamide, N-{[3-(2, 4-dimethoxyphenyl)-isoxazol-5-yl] methyl}-11-deoxy- glycyrrhetinamide,
N-[(3-p-trifluoromethylphenyl-isoxazol-5-yl) methyl]-11-deoxy- glycyrrhetinamide,
N-[(3-phenyl-isoxazol-5-yl) methyl]-11-deoxy-glycyrrhetinamide,
N-[(3-o-methoxyphenyl-isoxazol-5-yl) methyl]-3-acetoxy-glycyrrhetinamide,
N-[(3-o-methoxyphenyl-isoxazol-5-yl) methyl]-3-carboxymethoxy-glycyrrhetinamide,
N-[(3-o-chlorophenyl-isoxazol-5-yl) methyl]-3-ethoxy-glycyrrhetinamide,
N-[(3-p-methoxyphenyl-isoxazol-5-yl) methyl]-3-amino-11-deoxy-glycyrrhetinamide,
N-[(3-p-methoxyphenyl-isoxazol-5-yl)methyl]-3-diethylamino-11-deoxy-glycyrrhetinamide,
N-[(3-p-methoxyphenyl-isoxazol-5-yl) methyl]-3-acetylamino-11-deoxy-glycyrrhetinamide,
Sodium {N-[(3-o-methoxyphenyl-isoxazol-5-yl)methyl] glycyrrhetinamide-3-oxy}-acetate,
N-[(3-p-methoxyphenyl-isoxazol-5-yl)methyl]-3-ammonium-11-deoxy-glycyrrhetinamide hydrochloride,
N-[(3-p-methoxyphenyl-isoxazol-5-yl) methyl]-3-ammonium-11-deoxyglycyrrhetinamide acetate, and
Triethylammonium {N-[(3-o-methoxyphenyl-isoxazol-5-yl)methyl]glycyrrhetinamide-3-oxy}acetate;
or a pharmaceutically acceptable salt thereof.

4. A process for synthesizing the compounds of formula I according to claim 1, comprising the steps of
a. reacting a compound of formula IIa with zinc-amalgam in the presence of dioxane and hydrochloric acid to obtain a compound of formula IIb, and subjecting the compound of formula IIa or IIb to a chlorination reaction to obtain a compound of formula IIc

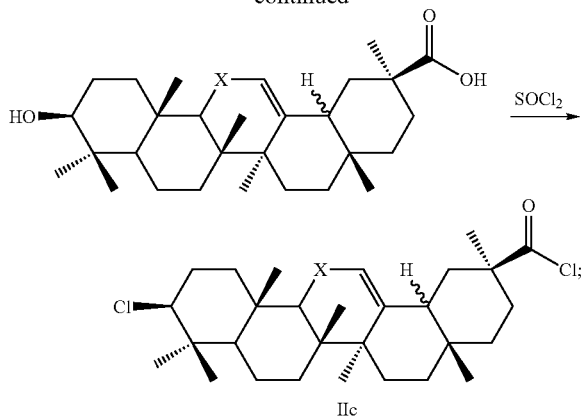

b. reacting a compound of formula IIIa, $R_2C=NOH$, with N-halo-succimide or sodium hypochlorite and then, in the presence of a base, with propargyl amine to obtain a compound of formula IIId; or
reacting a compound of formula IIIa, $R_2C=NOH$, with N-halo-succimide or sodium hypochlorite, and then, in the presence of a base, with propargyl alcohol to obtain a compound of formula IIIb, which is subjected to bromination to produce a compound of formula IIIc, which is in turn subjected to an aminolysis reaction to obtain a compound of formula IIId

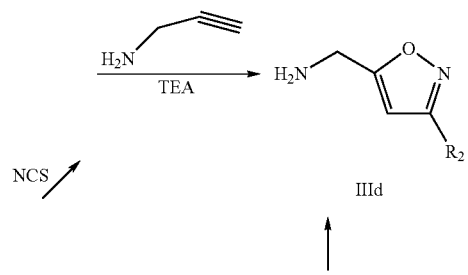

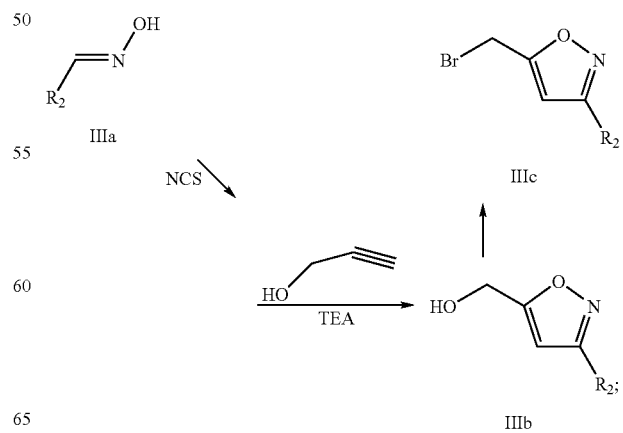

c. reacting the compound of formula IIId with the compound of formula IIa or IIb to obtain a compound of formula Ia

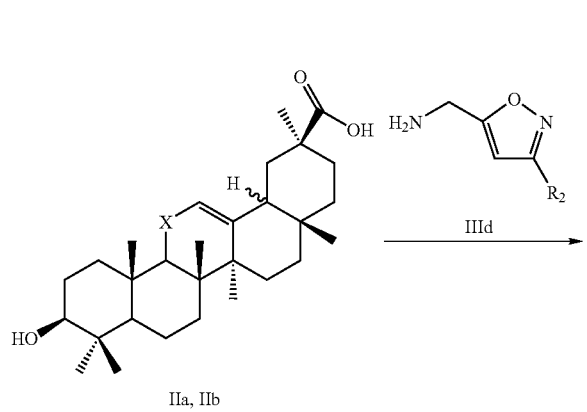

IIa, IIb or
reacting the compound of formula IIId with the compound of formula IIc to obtain a compound of formula Ib

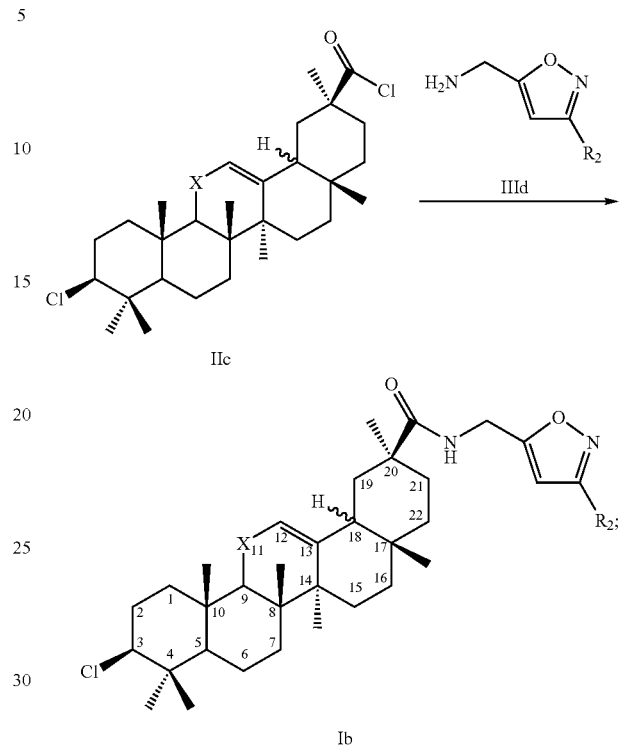

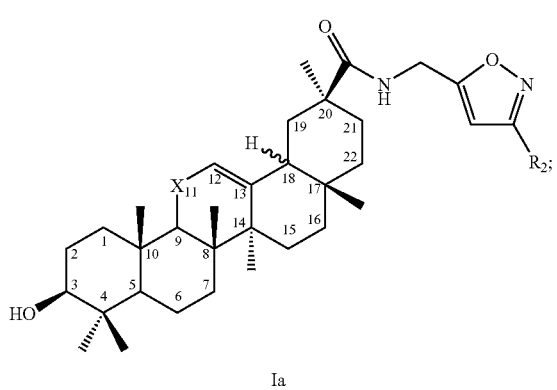

Ia wherein X and $R_2$ have the meanings as defined in claim 1, and, reacting the compound of formula Ia with an acetyl halide, a alkyl bromide, a carboxy-containing compound, or other reagents, or reacting the compound of formula Ib with ammonia, an amine, an alcohol or other reagents, to obtain other compounds of formula I.

5. A pharmaceutical composition, comprising the compounds of formula I or the pharmaceutically acceptable salt thereof according to claim 1, and an appropriate carrier or excipient.

6. The pharmaceutical composition according to claim 5, wherein said composition is in the form of a solid or liquid oral formulation, or an injection.

\* \* \* \* \*